United States Patent [19]

Pilipski

[11] 4,425,256

[45] Jan. 10, 1984

[54] CONVERSION OF CELLULOSE INTO ACTIVATED CHARCOAL

[75] Inventor: Mark Pilipski, Clifton, N.J.

[73] Assignee: Marcoal Chemical Industries, Clifton, N.J.

[21] Appl. No.: 355,883

[22] Filed: Mar. 8, 1982

Related U.S. Application Data

[63] Continuation-in-part of Ser. No. 108,057, Dec. 28, 1979, Pat. No. 4,318,710, which is a continuation-in-part of Ser. No. 62,980, Aug. 2, 1979, Pat. No. 4,260,685.

[51] Int. Cl.³ .................. B01J 20/20; C01B 31/08; C10L 9/02
[52] U.S. Cl. ............................. 502/418; 44/1 F; 44/10 C; 423/449; 502/180
[58] Field of Search ............ 44/1 F, 10 C, 1 R, 10 K; 252/444, 445, 422; 423/449, 460

[56] References Cited

U.S. PATENT DOCUMENTS

| | | | |
|---|---|---|---|
| 1,951,538 | 3/1934 | Tielens | 252/422 |
| 2,683,652 | 7/1954 | Martin | 423/460 X |
| 3,252,919 | 5/1966 | Bigelow, Jr. et al. | 423/460 X |
| 3,778,387 | 12/1973 | Urbanic et al. | 423/460 X |
| 3,832,306 | 8/1974 | Hackett et al. | 252/422 |
| 3,864,277 | 2/1975 | Kovach | 252/422 X |
| 3,998,756 | 12/1976 | Sutherland | 252/422 |
| 4,318,710 | 3/1982 | Pilipski | 44/1 F |

*Primary Examiner*—Carl F. Dees
*Attorney, Agent, or Firm*—Michael Ebert

[57] ABSTRACT

A process for converting wood stock or other cellulosic material into activated charcoal, use being made for this purpose of liquid anhydrous hydrogen chloride which converts the stock into a charcoal-like substance or charwood which is thereafter heated in a controlled atmosphere for a sufficient period to produce an activated charcoal.

8 Claims, No Drawings

CONVERSION OF CELLULOSE INTO ACTIVATED CHARCOAL

RELATED APPLICATION

This application is a continuation-in-part of my copending application Ser. No. 108,057, filed Dec. 28, 1979 now U.S. Pat. No. 4,318,710, entitled "Conversion of Cellulose into Charcoal," which in turn is a continuation-in-part of my copending application Ser. No. 062,980, filed Aug. 2, 1979 now U.S. Pat. No. 4,260,685 entitled "Saccharification of Cellulose," whose entire disclosure is incorporated herein by reference.

BACKGROUND OF INVENTION

This invention relates generally to a process for producing charcoal, and in particular to a technique wherein cellulosic stock is converted, without combustion, into charcoal by means of a catalytic agent.

Charcoal is a substance composed almost entirely of carbon, hydrogen, oxygen, this product being usually obtained by burning organic material in the absence of air by a destructive distillation technique. Because of its physical and chemical properties, charcoal yields a greater amount of heat in proportion to its volume than is obtainable from a corresponding quantity of wood. Moreover, as a fuel, it has the further advantage of being virtually smokeless.

Charcoal has a wide range of applications; for not only is it a valuable fuel, but it has metallurgical, chemical and various other practical uses. For economic reasons, the use of charcoal in metallurgy has given way to coke, but it remains an important material for the chemical industry. In its activated form it is useful as an adsorptive agent for the purification of gas and liquids.

In my above-identified copending application, cellulosic stock from any available source is subjected to hydrolysis by a liquid anhydrous chloride agent and converted thereby into glucose and other reducing substances. The glucose is then fermented to produce ethanol or ethyl alcohol, a valuable fuel as well as a solvent. In the present invention, the same agent or an agent having analogous chemical characteristics is used to effect conversion of cellulose into charcoal which is usable as a fuel or for any other known purpose.

Because billions of tons of carbon are fixed every year on the land area of the earth by photosynthesis, out of which about half appears in the form of cellulose, the ability to convert cellulose into almost pure carbon (i.e. charcoal) at low cost, affords a potential source of fuel of extraordinary magnitude. The fact that petroleum-derived hydrocarbon fuels are becoming increasingly scarce and much more expensive lends particular significance to this alternative source of fuel. Moreover, this source, which is derived from wood and other organic matter, is renewable and therefore effectively inexhaustible.

SUMMARY OF INVENTION

The main object of this invention is to provide a technique which entails no burning to convert cellulosic material into charcoal.

A significant feature of the invention is that the charcoal produced thereby has greater caloric value for a given amount of starting stock than that produced by conventional techniques.

More particularly, it is an object of this invention to provide a process for converting wood stock and any biomass having a significant cellulosic content into charcoal, conversion being effected at ambient temperatures by means of a catalyst constituted by liquid anhydrous hydrogen chloride or an agent having analogous chemical characteristics.

Also an object of this invention is to provide an efficient and economic technique of the above type which makes use of an agent which is not consumed in the reaction and which may be reconstituted and recycled.

DESCRIPTION OF INVENTION

I have found that by maintaining cellulosic stock such as pine sawdust, mechanical fiber, Kraft fiber or newspapers in a bath of liquid anhydrous hydrogen chloride beyond the time required for saccharification thereof, the wood is converted to a charcoal. As disclosed in my above-identified copending application, a woody substrate, when reacted for minutes in liquid anhydrous hydrogen chloride, yields sugars. I have discovered that this same woody substrate when kept in the bath of liquid anhydrous hydrogen chloride for several hours is converted to charcoal.

My tests show that when wood sawdust is exposed to liquid anhydrous hydrogen chloride it is converted into charcoal in less than 8 hours. On the other hand, the same amount of wood sawdust when exposed to gaseous anhydrous hydrogen chloride is also converted to charcoal; but in this instance, the completion of the conversion process takes more than a month. In both cases (using liquid or gaseous anhydrous hydrogen chloride) charcoal is produced at ambient temperatures.

I believe the relative rapidity of the reaction in liquid anhydrous hydrogen chloride as against the very slow conversion process when using gaseous anhydrous hydrogen chloride is due to the high density of this agent in the liquid state and its low density in the gaseous state. At slightly elevated temperatures, the reaction of cellulosic material with liquid anhydrous hydrogen chloride may be accelerated.

The introduction of cellulosic stock, such as pine sawdust, to liquid anhydrous hydrogen chloride gives rise to heat. I believe this exothermic reaction is due to the extraction and mixing of any small amount of water present within the cellulosic stock with the anhydrous hydrogen chloride. Any such water is immediately consumed by the hydrolytic saccharification of cellulose. After this initial heat is generated, the reaction appears to proceed without giving up any heat or requiring any measurable amounts of heat, as in an endothermic reaction.

After the charcoal has been formed, the hydrogen chloride must be purged from the charcoal. For this step, a dry stream of nitrogen is used to extract the hydrogen chloride from the produced charcoal. The purged hydrogen chloride is then recondensed for recycling. In practice, as an alternative to nitrogen any dry non-reactive gas or non-reactive fluid may be used to wash any residual hydrogen chloride from the charcoal. Thus hydrogen chloride is not consumed by the conversion process, and it is reclaimable.

I tested for residual chlorine compounds within the produced charcoal. Using KITAGAWA ® tubes and also a modified Fujiware test for this purpose, it was determined that less than 1 ppm of halogenated hydrocarbons was present in the charcoal. (This was the limit of detectability for these tests.)

In my test procedures, I tested for the presence of bromine, chlorine, chloroform, chlorobenzene, 1,2-dichloroethylene, ethylene chloride, hydrogen chloride, methyl bromide, methyl chloride, nitrogen dioxide, perchloroethylene, trichloroethylene, and vinyl chloride. I also sampled air drawn through the charcoal as well as effluent gases produced by heating the charcoal and also by burning the charcoal. I found no chlorine or chlorine compounds present in this charcoal or in its effluent gases. In summary, these tests indicated that there is no residual hydrogen chloride and no chlorinated hydrocarbons were present in charcoal produced by the action of anhydrous chloride upon cellulosic stock.

I also tested the charcoal produced by my process for the presence of chloride ions and found that those chloride ions present were matched in milliequivalents/liter to an almost equal amount of sodium ions, thereby indicating that any trace metals (sodium, magnesium, potassium, etc.) normally found in wood had been converted to chloride salts of these metals.

The charcoal produced by the action of anhydrous hydrogen chloride upon wood is soft and easily ground to a fine powder. This charcoal can be ground, packed, caked, or briquetted for ease of transportation. The produced charcoal occupies much less volume than the starting cellulosic stock, but its density is two to three times greater than the starting wood stock.

The caloric value of the charcoal produced by my process is equivalent to starting wood stock, which represents a distinct advantage over traditionally-produced charcoal. Before the 1900's, charcoal was the primary fuel for industrial processes. Charcoal was supplanted by coal and coke because the then-prevailing economic factors favored coal mining instead of the kiln-production of charcoal. Because the density of various coals is higher than the density of wood and charcoal, more coal can be shipped using fewer containers than are required to ship an equal weight of wood.

The traditional method for producing charcoal (destructive distillation) requires that wood be heated in an enclosed container or kiln whereby approximately one-half to two-thirds of the original fuel is gasified. As a consequence, usually more than half the original calories present in the wood stock are sacrificed in the traditional production of charcoal. Therefore, if one begins with one ton (2,000 lbs.) of wood and uses destructive distillation to manufacture charcoal, only 400-600 lbs. of charcoal are obtained. This charcoal would have a density of about twice that of the original wood. Some of the lost weight may be recovered by condensing many of the volatile hydrocarbons in the manner disclosed in the text, *Forest Energy and Economic Development* (D. E. Earl)-Clarendon Press, Oxford 1975 (page 34) during the early phases of destructive distillation. The fuel capacity of charcoal in terms of BTU/lb. produced by destructive distillation is about twice the value of the original wood stock.

By way of example, if we start with one ton of wood with a fuel capacity of approximately 5,700 BTU/lb., we would derive by destructive distillation 500 lbs. of charcoal with a fuel capacity of about 11,500 BTU/lb. Thus with the conventional destructive distillation technique, one starts with a potential 11.4 million BTU's and ends up with a potential 5.75 million BTU's. Hence in the traditional production of charcoal, nearly half of the potential fuel is destroyed.

Using my process (anhydrous hydrogen chloride), I have found that the BTU/lb. of the product charcoal is equivalent to the BTU/lb. of the original wood, as evidenced by the following results for four samples obtained when using the ASTM procedure D-2015.

Purpose

To determine the gross heat of combustion of the submitted samples.

Procedure

Tests were conducted in accordance with ASTM procedure D-2015. At the client's request, no sulfur correction was made.

Results

| Identification | Gross Heat of Combustion |
|---|---|
| Pine Sawdust | 11,778 BTU/lb. |
| Pine Sawdust post reaction | 11,756 BTU/lb. |
| Mechanical Fibre | 12,453 BTU/lb. |
| Mechanical Fibre post reaction | 13,518 BTU/lb. |

In short, my process changes the physical characteristics of the wood stock (for example, its density), but does not forfeit any of its potential fuel capacity.

The utilization of a modern fuel such as coke (which in essence is a charcoal-like substance produced from coal or oil) entails a technology that is completely compatible with the utilization of wood charcoal as a fuel. Therefore, no major redesign of furnaces is required to use charcoal as a fuel. Charcoal has an added advantage over coal or coke; this advantage being charcoal's low sulfur content. Indeed, charcoal when it is burned gives off virtually no sulfur compounds, no phosphorus compounds, or nitrogen oxides, the pollutants normally yielded by coal.

The above-identified pending application derives ethanol from cellulosic stock by first saccharifying the stock. If we convert only some of the original cellulosic stock to glucose and on to ethanol and further convert any remaining cellulose (not converted to glucose) to charcoal to provide the fuel required to effect distillation of the ethanol, ample fuel for such a procedure is present within the original cellulosic stock.

Roughly, if we start with a ton of wood stock (at ≈10,000 BTU/lb) and convert some percentage of that wood to glucose, say, 10%, and the remainder to charcoal, we can ferment the 200 lbs. of glucose into alcohol (150 lbs.). Distillation of this much ethanol requires, ideally, 60,000 BTU's. The alcohol produced would represent approximately 2,000,000 BTU's. The charcoal produced by the action of anhydrous hydrogen chloride would represent approximately 18,000,000 BTU's; thus more than enough to use for the distillation of the ethanol.

The process in accordance with the invention (using hydrogen chloride) to produce charcoal can also be used to carbonize many toxic wastes which now pose a health problem and are difficult to dispose. My process would be economically attractive because high pyrolysis temperatures are not required.

Other compounds besides hydrogen chloride will work for this process. Obviously, the other hydrogen halides will function as hydrogen chloride in this respect. It is believed that boron trichloride and boron trifluoride will also function as catalysts for my process.

Lithium chloride, in a molten state (this may be used to carbonize toxic organic wastes) will also function in the above described manner. I believe that chlorides having chlorine present with a valence of minus 1 ($-1$) will also function as catalysts; i.e.:

mercury chloride, HgCl
copper chloride, CuCl
boron trichloride, $BCl_3$
aluminum trichloride, $AlCl_3$
zinc chloride, $ZnCl_2$
cadmium chloride, $CdCl_2$
gallium chloride, $GaCl_3$
silicon chloride, $SiCl_4$
silver chloride, AgCl
gold chloride, AuCl

Charcoal and Charwood

The term "charcoal" is used herein in its conventional, generic sense. As defined in *Webster's Third New International Dictionary* (1971, G. & C. Merriam & Co.), charcoal is "1.a dark-colored or black porous form of carbon made from vegetable or animal substances (as from wood by charring in a kiln or retort from which air is excluded) and used for fuel and in various mechanical, artistic, and chemical processes."

I have found that the product formed by my technique wherein any cellulosic material or biomass is exposed to liquid anhydrous chloride or other hydrogen halide, at 0° C. to ambient temperatures, does indeed look and feel like soft charcoal. Actually, however, the product exhibits profound physiochemical and structural differences from wood or charcoal. These differences afford the basis for the derivation of a variety of other useful products.

The product formed by my process which by common usage may be called "charcoal" is in fact a "charwood." The term "charwood" has been coined to designate a product in accordance with the invention. This product is an unusually altered and densified form of wood which, to the best of my knowledge, is unlike anything found in nature or previously naturally-derived. Because of its unique physicochemical structure, composition and properties, I have found that charwood constitutes a potentially valuable source of a wide variety of substances.

Wood itself can be volatilized and used as a source of chemicals such as turpentine, tall oils, methanol, pyroligneous acids, etc. Wood can also be reduced to almost pure carbon and thence to activated carbon. I have discovered, however, that charwood is more easily susceptible to volatilization and organic extraction, and it requires much less energy input for activation.

Moreover, the destructive distillation of wood to produce charcoal is generally carried out in portable kilns and requires two to ten days to complete the process. When a retort is used, the condensed by-products consist of an aqueous mixture of wood tar and pyroligneous acid. After stripping of its wood spirit, the pyroligneous acid is then subjected to an azeotropic distillation to remove the water. The recovery of these by-products has become uneconomic because there are now cheaper methods of making methanol, acetic acid, and acetone. (see: *Manufactured Carbon*, by Davidson, H. W. Wiggs, PKC, Churchouse A. H., Maggs F. A. P., Bradley R. S.-Pergam on Press Ltd., 1968). In addition, the carbon hydrogen molar ratio of wood is in the neighborhood of C/H=0.55-0.65, whereas this ratio in my densified "charcoal" lies in the range of C/H=0.9.

A C/H ratio of close to 1 is considered nearly optimal for the liquefaction of hydrocarbons such as natural gas or naphtha (production of "synfuel"). A significant cost in present technology using coal or synthesis gas, is in achieving this ratio for optimal yields in the classic Fischer-Tropsch reaction. The water gas shift reaction is included as a means of adjusting the C/H ratio in the synthesis gas. (*Chemical & Engineering News*, Oct. 26, 1981). Accordingly, densified charwood produced by my process is potentially a valuable feedstock for synfuel production via some types of Fischer-Tropsch reactions and might well be superior economically in this regard to coal or synthetic gas.

Physicochemical Structure and Composition

Taking pine sawdust as the prototype substrate, I have found the chemical composition of the treated material (liquid anhydrous hydrogen chloride at 0° for 30 minutes to 2 hours) changes significantly as follows:

1. Mass balances using 10 gm. of pine sawdust show essentially no loss or gain in weight, pre- and post-treatment with liquid anhydrous hydrogen chloride or hydrogen fluoride. Most critical, the effluent hydrogen chloride was analyzed for water in gaseous reaction products ($\mu g/cm^3$ at 1 atm.) and negligible amounts were formed on three runs (30 minutes, 120 min. and 30 minute exposure): 1.4, 1.9, and 0.04 corresponding to 0.086%, 0.12% and 0.002%, respectively, comparable to the amounts found as contaminant in technical grade "anhydrous" HCl.

Together with evidence failing to show any significant amounts or organic chloride, these results lead me to conclude that the liquid anhydrous hydrogen halide is acting as a catalyst in the liquid phase, causing profund alteration in the physicochemical structure of the cellulosic material (pine sawdust, charwood, cotton, newsprint, Kraft paper, etc.).

2. Reducing sugars in small amounts (2-3%) are produced by the exposure process. There is some evidence that sugar yield increases with decreasing exposure time. Certainly, large amounts of sugar are produced at low temperatures, as described in my U.S. Pat. No. 4,260,685.

3. Infrared spectra films of methanol extract of the materials show that: The infrared spectra of the 3 reaction products are essentially similar, containing very broad bands of absorption centered around 3350, 1710, 1640, 1410, 1365, and 1035 cm$^{-1}$. The environment of the C-H bonds in the sawdust has been altered by the HCl treatment.

Examination by stereoscopic microscope revealed a shiny multicolored oil-like appearance in the interior of the treated samples as opposed to the duller grey exterior. Other volatile carbonaceous materials are present in all gas samples. The infrared spectra of KBr pellets of the reacted materials are essentially similar containing broad peaks centered at 3350, 2920, 1700, 1600, 1020, and 630 cm$^{-1}$.

The peaks at 2920 and 980-1180 cm$^{-1}$ are significantly smaller than the corresponding peaks in the unreacted material. This indicates a reduction of the absorbents of C-H and C-O-C bonds in the reaction products.

4. The bulk density of the materials measured in pentane is approximately twice that of the starting material.

5. Nuclear magnetic resonance spectra using an 8 Kz bandwidth with a 20 Hz window were performed on untreated and anhydrous HCl-treated pine sawdust, and clearly showed almost complete loss of glycosidic bonds and unsaturated carbons. This is consistent with the IR spectra showing reduction of C-O-C bonds. Selphen ($^{13}$C) runs confirmed and extended these findings. All of the NMR spectra demonstrated the appearance of broad peaks representing —$CH_2$— groups either aliphatic or aromatic and the presence of substituted aromatics. There was considerable loss of absorption of OH groups.

6. Photomicrographic evidence confirms and further describes some of the findings proven by physicochemical methods. These photomicrographs show that charwood displays alterations in the cellular matrix of the pine sawdust in the form of disruption of the cell walls. Under a polarizing microscope, deep inclusions containing refractile material are seen. Extraction with NaOH and tetrahydrofuran and heating causes further changes including deep pitting, shredding, and the appearance of punctate "bullet holes."

Thus a profound change in the physical and chemical nature of the cellulosic material (pine sawdust) occurs after exposure to liquid anhydrous hydrogen halide. All or most of the wood components seem to be retained although not in their original form, but in a total rearrangement or disarray, much the same as a collapsed building is related to the original structure.

Production of Activated Charwood

The commercial production of conventional activated carbon is an expensive and energy-intensive process. Thus, the present price for this substance ranges from 25¢/lb for the cheapest powdered material, to $2.50/lb and more for the granular specialty grades of activated carbon.

Two basic methods of activation are now in use. (*Manufactured Carbon,* 1968, Pergamon Press Ltd.). In the first, the raw material usually containing hydrogen and oxygen as well as carbon (anthacite coal, vegetable material, bone meal, wood, etc.) is carbonized (Temperature 500°–900° C. for 8 to 16 hours) and subsequently reacted with steam or water pressures in a special atmosphere of water vapor with or without hydrogen and carbon monoxide at 800°–900° C. for another several hours until a suitable degree of activation has been achieved. This is usually accompanied by a weight loss of 30–70%.

For chemical activation, the raw material is treated with solutions of activating chemicals; for example, strong mineral acids (HCl or phosphoric acid) or zinc chloride, and is then heated in an inert atmosphere at 600°–800° C. for several hours. The cooled solid is then leached (extracted) with water and/or acids and dried. The product is sometimes further activated with steam under pressure.

In one commercial process as disclosed in U.S. Pat. No. 2,977,325 (Feustel al.), use is made of peat coke drenched with sulfuric acid for 6 hours at ambient temperatures followed by heating at 500°–600° C. in reducing atmosphere for 24–48 hours.

In another process described in U.S. Pat. No. 4,149,955 (Murty), between fourteen and twenty steps are required to produce activated carbon from brown coal. These steps include removal of iron, crushing and screening pre-treated coal briquettes, treatment with inorganic acids, grinding of granules, compressng them into pellets at 40–80,000 psi, devolatization, then activating by heating in a special gaseous atmosphere, etc.

When "charwood" made in accordance with the invention is heated in a covered platinum crucible in a reducing atmosphere at a specified temperature (±10° C.) for thirty minutes, the following results were obtained:

| Temperature (°C.) | Weight Loss | Residue |
| --- | --- | --- |
| 200 | 15% | 85% |
| 400 | 36% | 64% |
| 500 | 47% | 53% |
| 600 | 57% | 43% |

Residue Analysis:

| | Residue at 200° C. | |
| --- | --- | --- |
| | Carbon | 68.49 |
| | Hydrogen | 2.08 |
| | Nitrogen | 0.79 |
| (difference) | Oxygen | 28.64 |
| | BTU (dry) | 10,990 BTU/lb |
| | Residue at 400° C. | |
| | Carbon | 73.88 |
| | Hydrogen ± | 3.55 |
| | Nitrogen | 0.13 |
| (difference) | Oxygen | 22.44 |
| | BTU (dry) | 12,325 BTU/lb. |

Further testing of charwood was performed after activation as follows:

ANALYSIS

The sample provided was activated by heating 4 hours at 500° C. followed by 4 hours at 750° C. under an initial/vacuum of 29.5. 50 grams of starting material yielded 14.5 grams of product. The following is a tabulation of the results of analyses run on the product:

ASH—3.16%
NITROGEN SURFACE AREA—585 m$^2$/g
IODINE #—470 mgI$_2$/g
MOISTURE ADSORPTION—8.24% in 5 hours 10.57% in 23 hours
APPARENT DENSITY— 0.192 on Unground Material   0.53 on Ball Milled Material*

| PARTICLE SIZE DISTRIBUTION | | |
| --- | --- | --- |
| | Before Milling | After Milling* |
| % Passing | 100 Mesh 4.2% | 85.3% |
| | 200 Mesh 1.4% | 55.8% |
| | 325 Mesh 0.1% | 39.6% |

*This sample was ball milled for ½ hour at 120 RPM.

65 grams of charwood was slurried with 2000 ml of distilled H$_2$O for 4 hours. The sample was filtered and dried at 100° C. for 24 hours. The washed sample was split into two 26 gram portions for activation.

One sample was heated under 29 inches of vacuum at 500° C. for 4 hours yielding 12.1 grams (46.5%), 11.1 grams of the 500° C. product was then heated at 750° C. for 4 hours yielding 7.3 grams (34.8% based on original 26 grams).

Another was heated under 29 inches of vacuum at 750° C. for 8 hours yielding 10.1 grams (38.8% based on original 26 grams).

Both final products were ground to −40 mesh in a Wiley mill. Samples were prepared at all stages for petrography. A series of 5 samples representing original sawdust, chemically treated sawdust, and three samples of chemically treated sawdust that were carbonized at varying temperatures, were briquetted with epoxy resin and polished for microscopic examination. These samples were examined optically using reflected light microscopy at high magnification to observe how each of these samples reacted to chemical treatment and subsequent heating. Maximum reflectance in air readings were also measured on each sample in order to:

a. Characterize the carbon response to various temperatures; and
b. Determine how the cracks and pores in the internal structure of the wood cell walls influenced the reflectance.

The study concentrated on the characteristics of the cell walls between the original wood cells. The central parts of the cells are preserved as structures with epoxy-filled pores, which were filled with volatile components in the original wood.

The cell walls are the only residue after chemical treatment and heating have occurred.

Upon microscopic observation of the samples, a general trend was noticed. As the sample was subject to increased heating, and therefore, increased carbonization, the reflectance in air was also observed to increase. This indicates a driving off the volatiles and an increase in the carbon content. The increase in brightness and reflectance, due to increased heating and carbonization, can also be seen in coal and other carbon products.

After chemical treatment and subsequent heating, changes in the structure of the walls between the original wood cells were apparent. It is possible that dehydration occurred as a result of the chemicals used in treatment, which produced abundant surface cracks and fracturing. As the sample underwent heating and carbonization (4 hours at 500° C.), cell wall porosity (up to an average of $5 \times 15\mu$) increased due to the development of the surface cracks and fracturing, while the reflectance increased also. Further heating of this sample (an additional 4 hours at 750° C.) caused an enlargement of the pores (up to an average of $7 \times 18\mu$), and a further increase in its reflectance in air. Another sample heated for eight hours at 750° C., shows an increase in larger pores (up to an average of $12 \times 15\mu$) with fewer small pores (an average of $4 \times 5\mu$). While the cell wall surfaces became more fractured and uneven, the maximum reflectance in air was still seen to increase.

The different rates of heating of the various samples appeared to influence the shapes and sizes of the pores in the cell walls. This is indicative of the devolatilization that occurs in the carbonization of organic materials. I observed only the structural differences of the cell walls as related to chemical treatment, temperature and rate of heating.

In summary, then, I have prepared by simple heating of "charwood" under vacuum or in a reducing atmosphere at 500° for four hours, 750° C. for four hours, or both, or at 900° C. for eight hours, an acceptable powdered activated carbon. This material approaches the AWWA Standard for use as an adsorption medium for the treatment of municipal and industrial water supplies. (ANSI/AWWA B600-78, *AWWA Standard For Powdered Activated Carbon,* American Water Works Association, 6666 West Quincy Avenue, Denver, Colorado 80235, Jan. 28, 1978.) Under different conditions, using other substrates, it should be possible to produce granulated activated carbon of equally good quality.

Briquetting and Slurries-Derivable Products

Densified wood produced by my process from hard or soft woods is so soft and friable that it can be crushed and reduced to a fine powder between the fingers. It is thus extremely compressible, and, in fact, with a simple mechanical cylinder I can reduce the volume three to four-fold. The resulting briquettes are quite firm, with or without an organic binder, and theoretically could yield up to 11,000–15,000 BTU's/lb. depending on the binder. Moreover, because of the compressibility and therefore increased density of the substance, the total BTU's per a given volume might well be more than twice that of coal. An obvious economic advantage would be reduction in cost of transport.

Furthermore, the ease of crushability or grinding compared, for example, with coal which contains silicates, iron, and other hard minerals, makes the production of slurries economically attractive. Thus water or other liquid slurries of charwood should be much more suitable and cheaper than coal for transport by pipeline.

Since charcoal in an oil slurry holds promise as fuel for steam boilers, I have experimented with finely divided charwood suspended in various types of light and heavy oils and liquid organic compounds and find these mixtures usable as a species of "liquid" fuel. Certainly the use of charwood suspensions would constitute a type of fuel extender especially if the volatiles were recycled and recombusted.

Extractable Organics

Charwood made in accordance with the invention was tested with twenty-four different solvents to see if anything could be extracted. I found that tetrahydrofuran, ethylene glycol, propylene glycol, cyclohexanone, methanol, ethanol, and butanol, in descending order, dissolve substances from charwood. Tetrahydrofuran is the most efficacious, removing about 15% of the dry weight. 5% NaOH removes another 15–20% by weight and is probably easily extracting lignings or substituted phenolics.

The tetrahydrofuran (THR) extract was further analyzed after recrystallization. This material did not melt but underwent charring at around 210° C. It was insoluble in carbon disulfide and incompletely soluble in carbon tetrachloride. Elemental analysis was as follows: N: 0.6%; C: 43.65%; H: 5.62%.

A solution spectrum in $CCl_4$ was taken; and after the appropriate peak assignments were made, the product seemed to have the following features:
- a carbonyl group from an aldehyde, ketone, carboxylic acid or ester
- an —O—H or amine group
- some unsaturation, probably due to the presence of aromatic rings
- possibly some ether linkages.

A thin layer chromatographic separation was attempted using a 1:1 mixture of chloroform and hexane as the solvent. Six bands were noted. Thus the THF extract contains more than one compound.

Volatiles

When charwood was volatilized at 200° in a reducing atmosphere for 90 minutes, acetic acid was positively identified by gas chromatography and mass spectroscopy. After pyrolysis, other volatiles analyzed by IR spectroscopy were tentatively identified as medium to high molecular weight polyfunctional aromatics. These might be phenols, aldehydes and ketones.

Hydrogen Halide Mixtures

In practice, one may use a mixture of hydrogen halides or other substances to adjust the boiling point, freezing point or density to optimize engineering conditions, thereby reducing the cost of producing charwood and products derivable therefrom.

I have measured the vapor pressure of mixture of HCL and HI and a mixture of anhydrous HCl and HF and have plotted the 6 points that were observed on graph paper along with the vapor pressure versus temperature curves for pure HCl, HBr, HI, and HF:

| Temperatures | (75% HCl) (25% HI) | (75% HF) (25% HCl) |
|---|---|---|
| 20° C. | 700 psi | 100 psi |
| 0° C. | 450 psi | 63 psi |
| −80° C. | 30 psi | 16 psi |

It can be seen, therefore that the vapor pressure vs. temperature relationships may be altered by combining various hydrogen halide gases.

Thus we may alter the concentrations of hydrogen halides to adjust our reaction conditions for maximum yield of product and minimum energy or engineering requirements. For example, we can lower the operating pressure in a reaction vessel by using a mixture of HCl and HF rather than using pure HCl and still maintain a bath of liquid anhydrous hydrogen halide(s).

I believe this will also apply to substances that are soluble in our reactant. Therefore, the inclusion of lithium Chloride into a bath of anhydrous HCl allowing safer operating pressures during the reaction of HCl with the cellulosic feedstock.

We have already demonstrated that HF and HCl saccharify and/or react with wood. Therefore, we would expect a mixture of these two halides to do the same.

While there has been shown and described a preferred of conversion of cellulose into activated charcoal in accordance with the invention, it will be appreciated that many changes and modifications may be made therein without, however, departing from the essential spirit thereof.

I claim:

1. A technique for converting raw stock rich in cellulose to an activated charcoal-like substance or charwood comprising the steps of:
   A subjecting the stock to an anhydrous liquid hydrogen halide for a time period sufficient to convert the stock to charwood;
   B purging the halide from the resultant charwood; and
   C heating the purged charwood in a controlled atmosphere to prevent oxidation thereof at an elevated temperature for a period sufficient to produce a charwood having properties comparable to activated carbon suitable as an adsorption medium.

2. A technique as set forth in claim 1, wherein said atmosphere is vacuum.

3. A technique as set forth in claim 1, wherein said atmosphere is a reducing atmosphere.

4. A technique as set forth in claim 1, wherein said temperature is in a range of about 500° to 900° C.

5. A technique as set forth in claim 1, wherein said time period is in a range of about four to eight hours.

6. A technique as set forth in claim 1, wherein said halide is hydrogen chloride.

7. A technique as set forth in claim 1, wherein said halide is a mixture of hydrogen chloride and hydrogen fluoride.

8. A technique as set forth in claim 1, wherein said purging is effected by means of a non-reactive fluid to extract any residual hydrogen halide from the charwood.

* * * * *